United States Patent
Kim et al.

(10) Patent No.: US 9,738,886 B2
(45) Date of Patent: Aug. 22, 2017

(54) APPARATUS FOR PREPARING IMMOBILIZED-ENZYME BEADS AND METHOD FOR PREPARING IMMOBILIZED-ENZYME BEADS USING SAME

(71) Applicant: CJ CHEILJEDANG CORPORATION, Seoul (KR)

(72) Inventors: Soon Chul Kim, Incheon (KR); Seong Bo Kim, Seoul (KR); Jae Youn Lim, Suwon-si (KR); Kwang Jin An, Incheon (KR); Jin Ha Kim, Bucheon-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 115 days.

(21) Appl. No.: 14/401,780

(22) PCT Filed: May 10, 2013

(86) PCT No.: PCT/KR2013/004166
§ 371 (c)(1),
(2) Date: Nov. 17, 2014

(87) PCT Pub. No.: WO2013/172601
PCT Pub. Date: Nov. 21, 2013

(65) Prior Publication Data
US 2015/0125922 A1    May 7, 2015

(30) Foreign Application Priority Data
May 17, 2012 (KR) ........................ 10-2012-0052385

(51) Int. Cl.
*C12M 1/00* (2006.01)
*C12N 11/00* (2006.01)
*C12M 1/12* (2006.01)

(52) U.S. Cl.
CPC ............. *C12N 11/00* (2013.01); *C12M 21/14* (2013.01); *C12M 25/16* (2013.01)

(58) Field of Classification Search
CPC ...................................................... C12M 21/14
See application file for complete search history.

(56) References Cited

U.S. PATENT DOCUMENTS 4,639,423 A    1/1987 Kahlert et al.
4,828,997 A    5/1989 Yamaguchi et al.
(Continued)

FOREIGN PATENT DOCUMENTS

JP    58-162292 A    9/1983
JP    60-120986 A    6/1985
(Continued)

OTHER PUBLICATIONS

Lee et al., "Continuous Production of Uniform Calcium Alginate Beads by Sound Wave Induced Vibration," *J. Chem. Tech. Biotechnol.* 67:255-259, 1996.

*Primary Examiner* — Rosanne Kosson
(74) *Attorney, Agent, or Firm* — Seed IP Law Group LLP

(57) ABSTRACT

The present invention relates to an apparatus for preparing enzyme-immobilized beads used for preparation of tagatose, and a method for preparing enzyme-immobilized beads using the same. More specifically, the present invention relates to an apparatus for preparing enzyme-immobilized beads, comprising a nozzle with an inside diameter of 0.1-1 mm having a cylindrical lower end and comprising a cut-type liquid outlet (cut perpendicularly to the vertical axis of the nozzle) formed at the lower end, and a method for preparing enzyme-immobilized beads using the same.

16 Claims, 3 Drawing Sheets

(56) References Cited

U.S. PATENT DOCUMENTS

| | | | |
|---|---|---|---|
| 5,089,407 A | | 2/1992 | Baker et al. |
| 5,429,821 A | * | 7/1995 | Dorian .................... A01N 1/02 264/4.1 |
| 5,725,888 A | | 3/1998 | Scott et al. |

FOREIGN PATENT DOCUMENTS

| | | |
|---|---|---|
| JP | 04-253744 A | 9/1992 |
| JP | 06-141822 A | 5/1994 |
| JP | 2000-131005 A | 5/2000 |
| JP | 2002-253228 A | 9/2002 |
| KR | 2003-0088749 A | 11/2003 |
| KR | 2003-0092674 A | 12/2003 |
| KR | 2008-0047844 A | 5/2008 |

* cited by examiner

APPARATUS FOR PREPARING IMMOBILIZED-ENZYME BEADS AND METHOD FOR PREPARING IMMOBILIZED-ENZYME BEADS USING SAME

TECHNICAL FIELD

The present invention relates to an apparatus for preparing enzyme-immobilized beads used for preparation of tagatose, and a method for preparing enzyme-immobilized beads using the same.

More particularly, the present invention relates to an apparatus for preparing enzyme-immobilized beads, which includes a nozzle having an inner diameter of 0.1 mm to 1 mm and a cylindrical lower end and including a cut-type liquid outlet (cut perpendicularly to a vertical axis of the nozzle) formed at the lower end thereof, and a method for preparing enzyme-immobilized beads using the same.

BACKGROUND

Tagatose, an isomer of galactose, is low-calorie sweetener which is naturally produced. Although tagatose exhibits similar sweetness to sugar, that is, about 92% sweetness of sugar, tagatose is spotlighted as a sugar substitute since tagatose only has about 38% the calories of sugar and an about 4% the glycemic index (GI) of sugar.

Moreover, tagatose is an approved as Generally Recognized As Safe (GRAS) by the Food and Drug Administration (FDA) and thus permitted to be used as a sweetener for food, beverages, health food, diet additives and the like, and is known to have almost no side effects when ingested by humans and thus is anticipated to be widely used.

Methods for producing tagatose include a chemical method in which a chemical catalyst is used to isomerize galactose, and a biological method in which galactose is isomerized using an isomerase. Although the chemical method has advantages in terms of economic efficiency and yield, there are problems in that the chemical method requires chemical processes at high temperature and high pressure, has complicated processes, and causes industrial waste. Therefore, there is an increasing need for a biological method.

In the related art in relation to a technique for mass production of tagatose using an isomerase, Korean Patent No. 10-0872694 discloses a method for mass production of tagatose using an arabinose isomerase, and Korean Patent No. 10-0464061 discloses a method in which an isomerase is immobilized to an appropriate carrier, followed by introduction of galactose, thereby driving isomerization into tagatose.

However, since the biological method is more sensitive to reaction conditions than the chemical method, the biological method causes a great difference in process efficiency, final yield, and the like when the reaction conditions are adjusted. In addition, when using an isomerase immobilized to a carrier, properties of the prepared carrier and a degree of immobilization vary according to apparatuses used in immobilization and methods of immobilization, thereby making it difficult to determine process efficiency, production yield and the like, and obstructing active use of the biological method.

Therefore, there are needs for an apparatus for preparing enzyme-immobilized beads optimized for stable mass production of tagatose through the biological method, and for a method for effectively immobilizing an isomerase or microbial cells capable of producing the isomerase to a carrier.

DISCLOSURE

Summary of the Invention

Technical Problem

It is an object of the present invention to provide an apparatus for preparing enzyme-immobilized beads used in preparation of tagatose, and a method for preparing enzyme-immobilized beads using the same.

More particularly, the present invention is aimed at providing an apparatus for preparing enzyme-immobilized beads, which includes a nozzle having an inner diameter of 0.1 mm to 1 mm and a cylindrical lower end and including a cut-type liquid outlet (cut perpendicularly to a vertical axis of the nozzle) formed at the lower end.

It is another object of the present invention to provide a method for preparing enzyme-immobilized beads optimized for isomerization through appropriate adjustment of the shape and size thereof.

Technical Solution

The present invention relates to an apparatus for preparing beads to which an enzyme and/or microbial cells capable of producing the enzyme are immobilized, and a method for preparing enzyme-immobilized beads using the same.

In accordance with one aspect of the present invention, an apparatus for preparing enzyme-immobilized beads includes: a) a first tank into which a mixed liquid containing an enzyme-containing material and an excipient is injected; b) a nozzle unit disposed at a lower end of the first tank, and comprising a nozzle which has an inner diameter of 0.1 mm to 1 mm and a cylindrical lower end and includes a liquid outlet cut perpendicularly to a vertical axis of the nozzle at the lower end thereof; and c) a second tank disposed below the nozzle unit and containing a calcium chloride solution.

A distance between a surface of the calcium chloride solution in the second tank and the liquid outlet of the nozzle unit may range from 0.1 m to 1.5 m.

The nozzle unit may include at least two nozzles.

The first tank may include a mixed liquid and/or air inlet.

In accordance with another aspect of the present invention, there is provided a method for preparing enzyme-immobilized beads using the apparatus for preparing enzyme-immobilized beads according to the present invention.

The mixed liquid injected into the first tank may be adjusted to a viscosity of 3,000 cPs to 7,000 cPs, and a pressure of 0.1 kg/cm$^2$ to 3 kg/cm$^2$ may be applied to the air inlet of the first tank.

The enzyme-immobilized beads prepared by the method may have a spherical shape having a diameter of 0.5 mm to 3 mm.

Advantageous Effects

According to the present invention, since the apparatus for preparing enzyme-immobilized beads includes a nozzle which has an inner diameter of 0.1 mm to 1 mm and a cylindrical lower end and includes a cut-type liquid outlet (cut perpendicularly to a vertical axis of the nozzle) formed at the lower end, the enzyme-immobilized beads having a uniform and smooth spherical shape and uniform pores can be prepared.

DETAILED DESCRIPTION OF THE INVENTION

Figure 1:
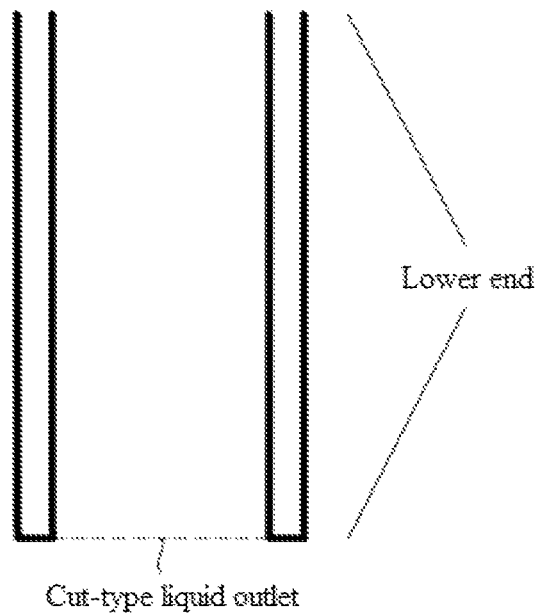
FIG. 1 is a schematic longitudinal sectional view of a lower end of a nozzle of an apparatus for preparing enzyme-immobilized beads according to one embodiment of the present invention.

Hereinafter, embodiments of the present invention will be described in detail with reference to the accompanying drawings. A description of details apparent to those skilled in the art will be omitted for clarity.

The present invention relates to an apparatus for preparing enzyme-immobilized beads used in preparation of tagatose and a method for preparing enzyme-immobilized beads using the same.

More particularly, the present invention relates to an apparatus for preparing enzyme-immobilized beads, which includes a nozzle having an inner diameter of 0.1 mm to 1 mm and a cylindrical lower end and including a cut-type liquid outlet (cut perpendicularly to a vertical axis of the nozzle) formed at the lower end, and a method for preparing enzyme-immobilized beads using the same.

According to one embodiment of the present invention, an apparatus for preparing enzyme-immobilized beads includes: a) a first tank into which a mixed liquid containing an enzyme-containing material and an excipient is injected; b) a nozzle unit disposed at a lower end of the first tank and including a nozzle, which has an inner diameter of 0.1 mm to 1 mm and a cylindrical lower end and includes a liquid outlet cut perpendicularly to a vertical axis of the nozzle at the lower end; and c) a second tank disposed below the nozzle unit and containing a calcium chloride solution.

The first tank may include a tank which can receive the mixed liquid containing the enzyme-containing material and the excipient, and an inlet through which the mixed liquid and/or air can be injected into the tank.

The mixed liquid injected into the first tank contains the enzyme-containing material and the excipient.

The enzyme-containing material refers to an isomerase per se, or a material containing microbial cells or dead microbial cells capable of producing the isomerase, and the isomerase refers to an enzymatic isomerization of galactose into tagatose and may be an arabinose isomerase.

In one embodiment, the microbial cells capable of producing the arabinose isomerase may include recombinant strains of the genus *Corynebacterium*.

The recombinant strains of the genus *Corynebacterium* may be recombinant including a gene coding the arabinose isomerase derived from *Thermotoga neapolitana* which is a hyperthermophile.

For details related to the recombinant strains of the genus *Corynebacterium* refer to Korean Patent No. 10-0872694.

In some embodiments, the excipient is preferably an alginate, more preferably an alginate solution in which an alginate is dissolved in a silicon dioxide solution.

According to the embodiment of the invention, the nozzle unit is disposed at the lower end of the first tank.

The nozzle unit may include at least one nozzle.

In some embodiment, the nozzle of the nozzle unit has a cylindrical lower end having an inner diameter from 0.1 mm to 1 mm, preferably from 0.2 mm to 0.5 mm, more preferably from 0.3 mm to 0.4 mm, and may include the cut-type liquid outlet formed at the lower end.

The liquid outlet means an outlet through which the mixed liquid injected into the first tank is discharged, and the cut-type liquid outlet means that the liquid outlet is formed by cutting the lower end of the nozzle in the perpendicular direction to the vertical axis of the nozzle (see FIG. 1 which is a longitudinal sectional view of the lower end of the nozzle).

Figure 4:
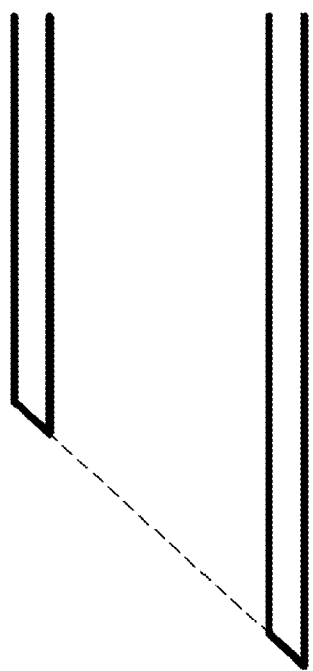
FIG. 4 is a schematic longitudinal sectional view of a lower end of an injection needle of a typical apparatus for preparing enzyme-immobilized beads.

A typical apparatus for preparing immobilized beads includes an injection needle (see FIG. 4) and is used to prepare pellet-type beads, thereby causing a problem of deterioration in isomerization efficiency. More specifically, when isomerization is performed using the pellet-type beads, a matrix liquid has a non-uniform moving load factor due to non-uniform pores when added, thereby causing deterioration in isomerization efficiency.

In contrast, when the nozzle according to the present invention, which includes the cut-type liquid outlet at the lower end thereof and has an inner diameter of 0.1 mm to 1 mm, is used, uniform and smooth spherical beads are prepared and thus provide uniform pores, whereby the matrix liquid can also have a uniform moving load factor, thereby preventing disproportional use of an enzyme due to a difference in pores in a filling tower (a facility used in isomerization by filling the facility with the enzyme-immobilized beads, followed by injection of the matrix liquid).

According to the present invention, the second tank includes a tank which can receive the calcium chloride solution, and an inlet into which the mixed liquid discharged from the nozzle unit is dropped and injected.

In some embodiments, a distance between a surface of the calcium chloride solution in the second tank and the liquid outlet of the nozzle unit preferably ranges from 0.1 m to 1.5 m, more preferably from 0.5 m to 0.8 m.

Within this range, since a dropping distance of the mixed liquid of the first tank from the nozzle unit can be appropriately adjusted, the mixed liquid can be formed into spherical beads while dropped and can be prevented from forming into elliptical beads due to collision with the surface of the calcium chloride solution in the event where the mixed liquid is dropped from an overly high place.

The apparatus for preparing enzyme-immobilized beads according to the embodiment of the invention will be described in more detail with reference to FIG. 2.

Figure 2:
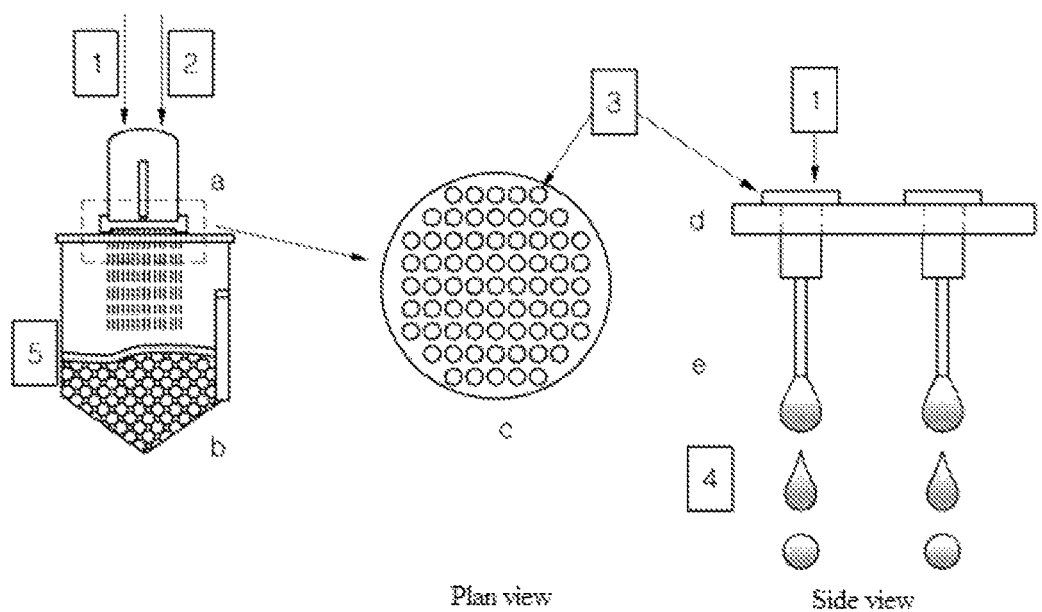
FIG. 2 is a schematic diagram of an apparatus for preparing enzyme-immobilized beads according to one embodiment of the present invention.

In FIG. 2, the apparatus for preparing enzyme-immobilized beads according to the embodiment of the present invention includes the first tank (a), the second tank (b), and the nozzle unit (c).

The first tank (a) includes a mixed liquid and/or air inlet disposed at an upper end thereof. The first tank (a) may include one or more inlets, which may be used together or separately.

The nozzle unit (c) is disposed at the lower end of the first tank (a) and may include at least one nozzle mounted therein.

Since the nozzle is provided at an upper end (d) thereof with a mixed liquid inlet, the mixed liquid is injected (1) into the nozzle through the mixed liquid inlet while air is injected (2) into the first tank (a). Since the nozzle has the cylindrical lower end (e) and includes the cut-type liquid outlet formed at the lower end thereof, immobilized beads discharged through the liquid outlet can be formed in a smooth and uniform spherical shape while dropped (4).

The immobilized beads discharged from the liquid outlet of the lower end of the nozzle are dropped (5) onto the calcium chloride solution contained in the second tank (b), and the distance between the lower end (e) of the nozzle and the surface of the calcium chloride solution in the second tank (b) may range from 0.5 m to 0.8 m.

According to one embodiment of the invention, a method for preparing enzyme-immobilized beads using the apparatus for preparing enzyme-immobilized beads according to the present invention is provided.

In preparation of enzyme-immobilized beads, a mixed liquid injected into the first tank may be prepared as follows: microbial cells capable of producing arabinose isomerase are killed, followed by centrifugation of a culture fluid of the microbial cells to recover dead microbial cells. Next, an alginate is dissolved to a concentration of 1.5% to 2.5% in a 0.4% to 1.0% silicon dioxide solution by stirring at 90±5° C. for 3 hours or more such that the alginate can be completely dissolved therein. After confirmation of complete dissolution of the alginate, the alginate solution is cooled to 35±5° C. by passing cooling water through a jacket. This process is performed to increase viscosity of the alginate while preventing damage to an enzyme upon mixing of microbial cells/enzyme.

Next, the separated microbial cells are mixed with the alginate solution using a stirrer at 30 rpm to 60 rpm. Due to high viscosity of the alginate solution, when the rotational speed becomes excessively high upon stirring, there occurs a phenomenon in which bubbles are generated inside the mixed liquid and do not float up to an upper side of the liquid and air flows into the beads during preparation of the beads due to the bubbles, causing the beads to float to the upper side of the liquid. Thus, the stirring speed is advantageously adjusted to 30 rpm to 60 rpm.

In preparation of the enzyme-immobilized beads, the mixed liquid injected into the first tank may have a viscosity of 3,000 cPs to 7,000 cPs. Within this range, uniform and smooth spherical beads can be prepared.

In some embodiments, in preparation of the enzyme-immobilized beads, when the mixed liquid is discharged through the nozzle, a pressure from 0.1 $kg/cm^2$ to 3 $kg/cm^2$, preferably from 0.5 $kg/cm^2$ to 2 $kg/cm^2$, more preferably from 0.7 $kg/cm^2$ to 1.7 $kg/cm^2$ is applied thereto through the air inlet of the first tank.

Within this range, the mixed liquid of the enzyme-containing material and the excipient can be passed in an appropriate amount through the nozzle and thus formed into the beads, and appropriate force can be applied to the mixed liquid while the mixed liquid is passed through the nozzle, whereby substantially spherical beads can be formed. As the shape of the beads is closer to a sphere, there are advantages in that the beads to which the enzyme is effectively immobilized can be obtained, and that subsequent isomerization can be efficiently performed due to an increased surface area of the beads.

According to the present invention, in preparation of the enzyme-immobilized beads, after the mixed liquid of the enzyme-containing material and the excipient is dropped onto the calcium chloride solution, injection of air into the calcium chloride solution may be further performed such that the immobilized beads can maintain a spherical shape.

Since there is a concern that the mixed liquid dropped onto the calcium chloride solution is pressed into a plate shape due to gravity and the beads pressed into the plate shape has low usability in isomerization due to a reduced surface area thereof, air may be injected into the calcium chloride solution to maintain the spherical shape of the beads.

A method for preparing tagatose using the apparatus for preparing enzyme-immobilized beads according to the present invention will be briefly described hereinafter.

1) Starter microorganisms are inoculated as a seed.
2) Microbial cells obtained through seed culture are subjected to primary fermentation.
3) After completion of primary fermentation, secondary fermentation is performed.
4) After completion of secondary fermentation, tertiary fermentation is performed.
5) After completion of tertiary fermentation, quaternary fermentation is performed.
6) After completion of quaternary fermentation, a surfactant is introduced, followed by heating to induce the microbial cells death.
7) The microbial cells are isolated through centrifugation.
8) The recovered microbial cells are mixed with an alginate and silicon dioxide.
9) The mixed liquid is introduced into an immobilization apparatus to form beads.
10) The beads are stabilized by soaking in a galactose solution.
11) The beads are transferred to a fluidized bed reactor to fill the reactor column with the beads.
12) A galactose solution is transferred to the fluidized bed reactor to perform conversion into tagatose.

In preparation of tagatose using the apparatus for preparing enzyme-immobilized beads according to the present invention, high-concentration and/or high-purity tagatose can be prepared. Advantageously, tagatose having a purity of 99% or more in terms of solid content can be prepared.

Hereinafter, the present invention will be explained in more detail with reference to some examples. However, it should be understood that these examples are provided for illustration only and are not to be construed in any way as limiting the present invention.

EXAMPLE 1

Preparation of Enzyme-Immobilized Beads (1) Preparation of Mixed Liquid of Enzyme-Containing Material and Excipient Microbial cells capable of producing an arabinose isomerase were killed, followed by centrifugation of a culture media of the microbial cells to recover the dead microbial cells. Next, an alginate was dissolved to a concentration of 2% in a 0.7% silicon dioxide solution by stirring at 90° C. for 3 hours or more such that the alginate could be completely dissolved in the solution. After confirmation of complete dissolution of the alginate, the alginate solution was cooled to 35° C. by passing cooling water through a jacket.

Next, the alginate solution and the separated microbial cells were mixed using a stirrer at 50 rpm.

(2) Discharge of Mixed Liquid

The mixed liquid was confirmed to have a viscosity of 5,000 cPs, followed by injection into a first tank. Next, the alginate/microbial cells-mixed liquid was passed through a nozzle having an inner diameter of 0.3 mm and a cut shape at a distal end thereof by supplying air at a pressure of 1.2 kg/cm², thereby dropping the mixed liquid in a spherical shape having a diameter of 1.7 mm onto a 1% calcium chloride solution contained in a second tank.

(3) Formation of Immobilized Beads

The beads discharged from the nozzle were dropped onto the calcium chloride solution separated from a liquid outlet of the nozzle by a distance of 0.6 m while supplying air onto the calcium chloride solution (air bubbling), and then transferred to a cooling tank, followed by curing at 2° C. for 24 hours.

Figure 3:
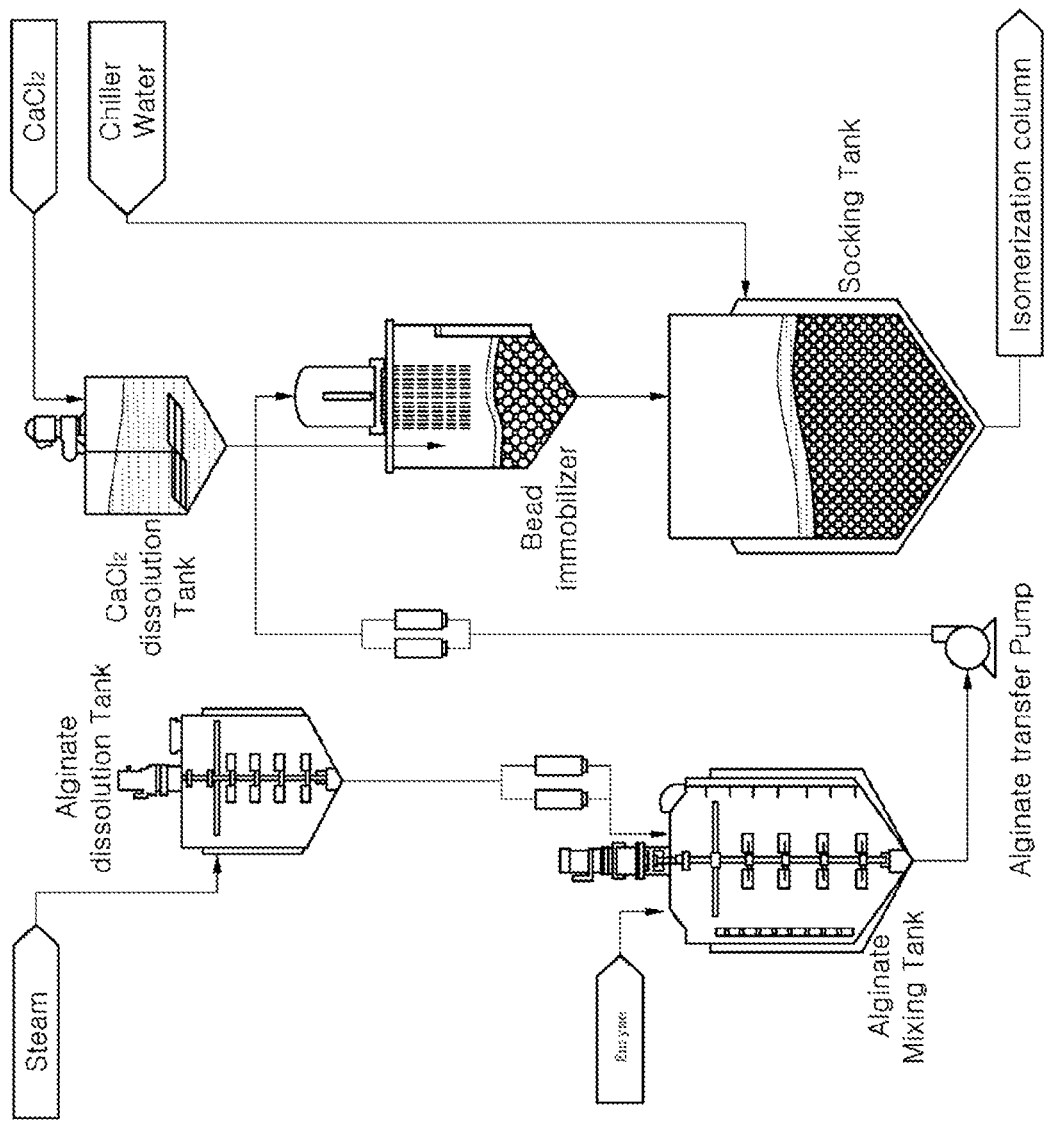
FIG. 3 is a schematic diagram showing a process and apparatus for preparing enzyme-immobilized beads.

A process and apparatus for preparing the enzyme-immobilized beads are shown in FIG. 3.

LIST OF REFERENCE NUMERALS

[Apparatus]
a: First tank
b: Second tank
c: Nozzle unit
d: Upper end of nozzle
e: Lower end of nozzle
[Process]
1: Inject mixed liquid
2: Inject air
3: Inject mixed liquid into mixed liquid inlet of upper end of nozzle
4: Discharge and drop immobilized beads from liquid outlet of lower end of nozzle
5: Drop immobilized beads onto calcium chloride solution in second tank

The invention claimed is:

1. An apparatus for preparing immobilized-enzyme beads, comprising:
  a) a first tank into which a mixed liquid containing an enzyme-containing material and an excipient is injected;
  b) a nozzle unit disposed at a lower end of the first tank and comprising a nozzle, the nozzle having an inner diameter of 0.1 mm to 1 mm and a cylindrical lower end and including a liquid outlet cut perpendicularly to a vertical axis of the nozzle at the lower end thereof; and
  c) a second tank disposed below the nozzle unit and containing a calcium chloride solution,
  wherein the distance between the surface of the calcium chloride solution in the second tank and the liquid outlet of the nozzle unit ranges from 0.1 m to 1.5 m.

2. The apparatus according to claim 1, wherein the nozzle unit comprises at least two nozzles.

3. The apparatus according to claim 1, wherein the first tank comprises an air inlet.

4. A method for preparing immobilized-enzyme beads using the apparatus for preparing immobilized-enzyme beads according to claim 1, wherein the method comprises: dropping the mixed liquid in the first tank through the nozzle unit onto the calcium chloride solution, thereby preparing immobilized-enzyme beads.

5. The method according to claim 4, wherein the mixed liquid injected into the first tank is adjusted to a viscosity of 3,000 cPs to 7,000 cPs.

6. The method according to claim 4, wherein the enzyme-immobilized beads have a spherical shape having a diameter of 0.5 mm to 3 mm.

7. A method for preparing immobilized-enzyme beads using the apparatus for preparing immobilized-enzyme beads according to claim 2, wherein the method comprises: dropping the mixed liquid in the first tank through the nozzle unit onto the calcium chloride solution, thereby preparing immobilized-enzyme beads.

8. The method according to claim 7, wherein the mixed liquid injected into the first tank is adjusted to a viscosity of 3,000 cPs to 7,000 cPs.

9. The method according to claim 7, wherein the enzyme-immobilized beads have a spherical shape having a diameter of 0.5 mm to 3 mm.

10. A method for preparing immobilized-enzyme beads using the apparatus for preparing immobilized-enzyme beads according to claim 3, wherein the method comprises: dropping the mixed liquid in the first tank through the nozzle unit onto the calcium chloride solution, thereby preparing immobilized-enzyme beads.

11. The method according to claim 10, wherein the mixed liquid injected into the first tank is adjusted to a viscosity of 3,000 cPs to 7,000 cPs, and a pressure of 0.1 kg/cm² to 3 kg/cm² is applied to the air inlet of the first tank.

12. The method according to claim 10, wherein the enzyme-immobilized beads have a spherical shape having a diameter of 0.5 mm to 3 mm.

13. The apparatus of claim 1, wherein the excipient is an alginate.

14. The method of claim 4, wherein the excipient is an alginate.

15. The method of claim 7, wherein the excipient is an alginate.

16. The method of claim 10, wherein the excipient is an alginate.

* * * * *